United States Patent [19]

Woo et al.

[11] Patent Number: 5,674,703
[45] Date of Patent: Oct. 7, 1997

[54] EPISOMAL VECTOR SYSTEMS AND RELATED METHODS

[76] Inventors: Savio L. C. Woo, 5343 Rutherglenn, Houston, Tex. 77096; Peter W. Nordloh, 1104 S. 8th St., Burlington, Iowa 52601; Arne Stenlund, 1 Bungtown Rd., Cold Spring Harbor, N.Y. 11724

[21] Appl. No.: 161,286

[22] Filed: Dec. 2, 1993

Related U.S. Application Data

[63] Continuation-in-part of Ser. No. 984,400, Dec. 2, 1992, abandoned.
[51] Int. Cl.$^6$ .......................... C12P 21/06; C12P 21/02; C12P 21/04; C12N 15/00
[52] U.S. Cl. .................. 435/69.1; 435/69.1; 435/69.4; 435/69.5; 435/69.6; 435/70.1; 435/240.1; 435/320.1; 935/60
[58] Field of Search ...................... 435/320.1, 69.1, 435/69.4, 69.5, 69.6, 70.1, 240.1; 935/60; 424/93.2; 514/44

[56] References Cited

PUBLICATIONS

Baker and Howley, "Differential Promoter Utilization by the Bovine Papillomavirus in Transformed Cells and Productively Infected Wart Tissues", 6(4) *EMBO J.* 1027, 1987.
Chen et al., "The Primary Structure and Genetic Organization of the bovine Papillomavirus Type 1 Genome", 299 *Nature* 529, 1987.
Ledley, "Somatic Gene Therapy for Human Disease: Background and Prospects. Part 1", 110(1) *J. Pediatrics* 1, 1987.
Lusky et al., "A Bovine Papilloma Virus Type 1—Encoded Modulator Function is Dispensable for Transient Viral Replication But is Required for Establishment of the Stable Plasmid Site", 60(2) *J. Virology* 729, 1986.
Sarver et al., "Bovine Papilloma Virus Deoxyribonucleic Acid: A Novel Eucaryotic Cloning Vectro", 1(6) *Molec. Cell Biol.* 486, 1981.
Spalholz et al., "Transactivation of a Bovine Papilloma Virus Transcriptional Regulatory Element by the E2 Gene Product", 42 *Cell* 183, 1985.
Ustav et al., "Identification of the Origin of Replication of Bovine Papillomavirus and characterization of the Viral Orgin Recognition Factor E1", 10 (13) *EMBO J.* 4321, 1991.
Ustav and Stenlund, "Transient Replication of BPV-1 Requires Two viral Polypeptides Encoded by the E1 and E2 Open Reading Frames", 10(2) *EMBO J.* 449, 1991.
Culver et al., "In vivo Gene Transfer with Retroviral Vectro–Producer Cells for Treatment of Experimental Brain Tumors", 256 *Science* 1550, 1992.
Lusky et al., "Characterization of the Bovine Papilloma Virus Plasmid Maintenance Sequences", 36(2) *Cell* 391, 1984.

*Primary Examiner*—Deborah Chouch
*Attorney, Agent, or Firm*—Lyon & Lyon LLP

[57] ABSTRACT

An episomal vector sytem and methods for use in gene therapy in humans and animals. The vector contains a papilloma virus origin of replication, a vector maintenance sequence, a first promoter transcriptionally linked to a therapeutic nucleic acid sequence, a second promoter transcriptionally linked to a papilloma virus E1 gene sequence, and a third promoter transcriptionally linked to a papilloma virus E2 gene sequence or an E1/E2 fusion gene. The vector is capable of episomal replication in human or animal cells.

39 Claims, 4 Drawing Sheets

EPISOMAL VECTOR SYSTEMS AND RELATED METHODS

RELATED APPLICATION

This application is a continuation-in-part of Woo et al., U.S. patent application Ser. No. 07/984,400, filed Dec. 2, 1992, now abandoned entitled "Episomal Vectors for Gene Therapy", the whole of which (including drawings) is hereby incorporated by reference.

The invention was partially supported by a grant from the United States under DK-44080 awarded by the National Institute of Health. The government may have certain rights in the invention.

BACKGROUND OF THE INVENTION

The present invention relates generally to episomal vector systems for gene therapy and methods of attaining episomal vector replication in human and other animal cells. The episomal vector systems contain papilloma virus nucleic acid sequences.

The papillomaviruses are widely found in nature and have been recognized primarily in higher vertebrates. They have been characterized from cattle, rabbits, horses, dogs, sheep, elk, deer, nonhuman primates, the harvest mouse, the multimammate mouse and humans. Over 50 distinct human papilloma viruses ("HPV") have been described. Genomic sequences of several of these, including HPV-1, HPV-11, HPV-16 and HPV-18 have been determined.

The papillomaviruses are highly species specific and have a specific tropism for squamous cells. Viral replication is restricted to the most terminally differentiated keratinocytes of the epithelium, although viral DNA can be found within basal and parabasal cells of a papilloma. Viral transcripts have been found in the basal cells of the epidermis, but late gene expression occurs only in the terminally differentiated cells. Thus, viral replication is latent in basal cells and productive in the more terminally differentiated cells within the upper layers of the epithelium.

Papillomaviruses encode trans-acting factors that modulate viral transcription. The first of these factors to be described was the E2 protein. The E2 Open Reading Frame ("ORF") contains domains that are relatively well-conserved among the papillomaviruses. E2 proteins are DNA-binding proteins which consist of two highly conserved domains joined by a more degenerate central region which is considered to be a linker region. Limited homology of E2 protein with the cellular oncogene c-mos has been noted.

There is a subgroup of papilloma viruses, which includes Bovine papilloma virus type 1 ("BPV-1") that can readily transform a variety of rodent cells in culture. BPV-1 is a small, non-enveloped, icosahedral DNA virus which causes cutaneous fibropapillomas in cattle and an equine sarcoid tumor in horses. The BPV-1 genome is a double stranded, closed circle of 7,945 base pairs. The entire sequence is known. The virus infects both dermal fibroblasts and epidermal epithelial cells but viral particles are produced only in terminally differentiated epidermal keratinocytes. Currently there are no means to propagate the virus in culture. The cloned viral DNA can transform mouse C127I fibroblasts in culture in which the viral DNA is maintained as a multicopy extrachromosomal nuclear plasmid with a stable copy number of 50–100 copies per cell.

A 5.4 kb subgenomic fragment of the viral genome (referred to as the '69% region') is sufficient for transformation of C127I cells in vitro and contains all eight of the viral open reading frames. At the 5' end of the 69% fragment there is a 1 kb stretch devoid of open reading frames referred to as the upstream regulatory region. This region contains several promoters/enhancers and the viral origin of replication. In cells transformed by the virus, only a few of the viral open reading frames are expressed. The viral origin of replication has been mapped and sequenced. The human papilloma viruses contain genes and replication control sequences similar to those found in BPV-1 and other papilloma viruses.

SUMMARY OF THE INVENTION

The present invention provides papilloma virus episomal vector systems and methods for papilloma virus episomal vector replication in a variety of human and animal cells not normally permissive for replication of a particular papilloma virus or for maintenance of a particular papilloma virus sequence. There are provided episomal vector systems containing papilloma virus E1 and E2 genes and a papilloma virus origin of replication. These vectors are capable of episomal replication and due to their small size allow for insertion of a therapeutic nucleic acid sequence, which may be efficiently expressed in a human or other animal cell.

In a first aspect the invention features an episomal vector system for gene therapy in humans or animals which contains a polyfunctional nucleic acid sequence from a papilloma virus, the polyfunctional nucleic acid sequence including an origin of replication, a vector maintenance sequence, a first promoter and a unique restriction site for insertion of one or more therapeutic nucleic acid sequences; a first expression cassette containing a papilloma E1 gene sequence and a second promoter to drive transcription of the E1 gene; a second expression cassette containing a papilloma E2 gene sequence and a third promoter to drive transcription of the E2 gene; the first and second expression cassettes cloned into an episomal vector; and the episomal vector system includes one or more episomal vectors, each capable of episomal replication in a human or other animal cell.

In a preferred embodiment this invention features an episomal vector system for gene therapy in humans or animals which contains a polyfunctional nucleic acid sequence from BPV-1 (nucleotides 4780 to 471 from the BPV-1 genome, (e.g., 3636 bp in length)) in a vector, SEQ. ID. NO. 1, the polyfunctional nucleic acid sequence including an origin of replication, a vector maintenance sequence, a first promoter and a unique restriction site for insertion of one or more therapeutic nucleic acid sequences; a first expression cassette containing a BPV-1 E1 gene sequence, SEQ. ID. NO. 2, and a second promoter to drive transcription of the E1 gene; a second expression cassette containing the BPV-1 E2 gene sequence, SEQ. ID. NO. 3, and a third promoter to drive transcription of the E2 gene; the first and second expression cassettes cloned into an episomal vector; and the episomal vector system includes one or more episomal vectors each, capable of episomal replication in a human or animal cell.

In another preferred embodiment this invention features an episomal vector system for gene therapy in humans or animals which contains a polyfunctional nucleic acid sequence from a Human papilloma virus ("HPV") in a vector, the polyfunctional nucleic acid sequence including an origin of replication, a vector maintenance sequence, a first promoter and a unique restriction site for insertion of one or more therapeutic nucleic acid sequences; a first expression cassette containing a HPV E1 gene sequence and a second promoter to drive transcription of the E1 gene; a second expression cassette containing a HPV E2 gene sequence and a third promoter to drive transcription of the E2 gene; the first and second expression cassettes cloned into a vector; and the episomal vector system includes one or more episomal vectors each, capable of episomal replication in a human or animal cell.

The term "vector" as used herein refers to nucleic acid derived from a plasmid, cosmid, phagemid or bacteriophage, into which fragments of nucleic acid may be inserted or cloned. The vector can contain one or more unique restriction sites for this purpose, and may be capable of autonomous replication in a defined host or organism such that the cloned sequence is reproduced. The vector molecule can confer some well-defined phenotype on the host organism which is either selectable or readily detected. Some components of a vector may be a DNA molecule further incorporating a DNA sequence encoding regulatory elements for transcription, translation, RNA stability and replication.

The term "origin of replication" refers to a papilloma virus DNA sequence at which nucleic acid, typically DNA, synthesis is initiated. The minimal sequence for the BPV-1 origin of replication is defined by a 41 nucleotide sequence containing bases 7935 to 30. Those of ordinary skill in the art can determine other minimum sequences in other papilloma viruses using routine procedures.

The term "vector maintenance sequence" refers to a cis-acting nucleic acid sequence contained in a vector and which confers long term stable vector replication to the vector. A vector containing a vector (plasmid) maintenance sequence will remain unrearragned and stably maintained at a constant copy number. See Lusky, M. et al., Characterization of the Bovine Papilloma Virus Plasmid Maintenance Sequences. *Cell* 36(2) 391–401 (1984).

The term "therapeutic nucleic acid sequence" as used herein refers to a genetic material of interest which expresses a protein, polypeptide or RNA when incorporated into the cell of an animal or human. A therapeutic nucleic acid sequence is positionally and sequentially oriented within the episomal vector with other necessary elements such that the therapeutic nucleic acid sequence or sequences can be transcribed and when necessary translated into the cells in which the episomal vector has been incorporated. Other elements can include promoters, introns, untranslated regions, non-coding regions, regulatory regions, etc. One skilled in the art will be able to determine the specific necessary elements for each specific sequence and application.

The genetic material which is incorporated into the therapeutic nucleic acid sequence or sequences can be any DNA or RNA. For example, the nucleic acid can be: (1) not normally found in the tissues of the cell; (2) normally found in a specific tissue but not expressed at physiologically significant levels; (3) normally found in specific tissue and normally expressed at physiological levels in the specific tissue; (4) any other DNA or RNA which can be modified for expression in a specific tissue and (5) any combination of the above.

Examples of some therapeutic nucleic acid sequences which may be incorporated in an episomal vector includes the following. Therapeutic nucleic acid sequences selected from the group consisting of nucleic acid sequences encoding receptors, enzymes, ligands, regulatory factors, and structural proteins. Therapeutic nucleic acid sequences selected from the group consisting of nucleic acid sequences encoding nuclear proteins, cytoplasmic proteins mitochondrial proteins, secreted proteins, plasmalemma-associated proteins, serum proteins, viral antigens, bacterial antigens, protozoal antigens and parasitic antigens. Therapeutic nucleic acid sequences selected from the group consisting of nucleic acid sequences encoding proteins, lipoproteins, glycoproteins, phosphoproteins and nucleic acid. Proteins or polypeptides which can be expressed using the episomal vector of the present invention include hormones, growth factors, enzymes, clotting factors, apolipoproteins, receptors, drugs, oncogenes, tumor antigens, tumor suppressors, viral antigens, parasitic antigens and bacterial antigens. Specific examples of these compounds include proinsulin, insulin, growth hormone, androgen receptors, insulin-like growth factor I, insulin-like growth factor II, insulin-like growth factor binding proteins, epidermal growth factor TGF-α, TGF-β, PDGF, angiogenesis factors (acidic fibroblast growth factor, basic fibroblast growth factor and angiogenin), matrix proteins (Type IV collagen, Type VII collagen, laminin), phenylalaninehydroxylase, tyrosinehydroxylase, oncogenes (ras, fos, myc, erb, src, sis, jun), E6 or E7 transforming sequence, p53 protein, Rb gene product, cytokine receptor, IL-1, IL-6, IL-8, viral capsid protein, and proteins from viral, bacterial and parasitic organisms which can be used to induce an immunologic response, and other proteins of useful significance in the body. The compounds which can be incorporated are only limited by the availability of the nucleic acid sequence for the protein or polypeptide to be incorporated. One skilled in the art will readily recognize that as more proteins and polypeptides become identified they can be integrated into the episomal vector and expressed in the animal or human tissue.

The term "expression cassette" as used herein refers to a nucleic acid sequence which is capable of being transcribed and translated to result in production of a polypeptide.

The term "E1 gene sequence" as used herein means a gene which encodes the E1 polypeptide which is the protein product of the E1 open reading frame of a papillomavirus. The E1 protein possesses the ability to bind to homologous or heterologous a cis-acting DNA sequence, e.g., a papillomavirus origin of replication region, thereby targeting this region for the initiation of DNA synthesis by cellular DNA-synthesis proteins.

The term "E2 gene, sequence" as used herein means a gene which encodes the E2 polypeptide which is the protein product of the E2 open reading frame of a papillomavirus. The E2 protein possesses the ability to trans-activate, in the presence of the papillomavirus E1 protein, the replication of homologous or heterologous DNA containing a cis-acting DNA sequence, e.g., a papillomavirus origin of replication region, by cellular DNA-synthesis proteins.

Further, any such nucleic acid sequence which encodes a portion of an E1 or E2 protein which exhibits the functional characteristics of an E1 or E2 protein as defined above are within the preferred embodiment. These protein sequences comprising less than a whole E1 or E2 protein but which are nevertheless functional, may be mapped by mutational analysis or various clones may be created and the activity of proteins expressed from such clones assayed or other routine testing as is known in the art may be utilized.

In another preferred embodiment the first and/or second and/or third promoter may be asteroid regulated promoter, regulatable by asteroid hormone receptor gene switch as set forth in United States patent application entitled "Mutated Steroid Hormone Receptors, Methods for their Use and Molecular Switch for Gene Therapy" filed Sep. 2, 1993, Ser. No. 07/939,246, incorporated herein by reference. By including these steroid regulatable elements, the administration of a steroid hormone analog will induce episomal replication. Cessation of administration of the steroid hormone will result in the cessation of episomal vector replication. The episomal vector systems of this invention have a discrete half-life. Once replication of the episomal vectors has ceased, degradation of the episomal vectors results in the effective elimination of the episomal vector from the human or other animal cell in which it was contained. Alternatively, other methods of regulating the replication of the episomal vectors, by the administration of a substance which activates an administered-compound-regulatable promoter are within the scope of the present invention. By "administered-compound-regulatable promoter" is meant a promoter which is activated in response to a exogenously administered substance, where the administered substance is not typically present in a human or other animal.

In another embodiment, an episomal vector containing a thymidine kinase gene may be administered. Upon administration a substrate for thymidine kinase, as is known in the art, a toxic, phosphorylated nucleic acid base is generated which results in cell death, effectively causing the cessation of production of any other gene product contained in an administered episomal vector.

In specific embodiments of the present invention the first, second or third promoters can be identical or can be different when the promoter is from a ubiquitously expressed gene. Specific examples of ubiquitously expressing promoters include phosphoglycerolkinase, Rous Sarcoma Virus Long Terminal Repeat ("RSV-LTR"), Immediate Early Cytomegalovirus ("IE-CMV") or dihydrofolate reductase ("DHFR") promoters.

In specific embodiments of the present invention the first, second and third promoters can be identical or can be different when the promoter is from a gene expressed in a tissue-specific manner. However, where the tissue-specific promoters are different, they must all be capable of providing expression in a specific tissue type. For example three different liver specific promoters may be utilized. Examples of tissue-specific promoters include creatine kinase promoter, insulin promoter, immunoglobulin heavy chain promoter/enhancer, albumin enhancer/promoter, tyrosine aminotransferase promoter, transferrin promoter, cytochrome P-450 promoter, apolipoprotein E promoter, apolipoprotein A-1 promoter and β-actin promoter for liver expression, elastin, alpha-1 (I) collagen, keratin K1, K6 and loricrin for skin expression; alpha actin, beta myosin heavy chain, myosin light chain, aldolase A for muscle expression; type 4 collagenase, Clara protein, serine dehydratase for lung expression; myelin basic protein, beta amyloid precursor protein, glutamine synthetase, tyrosine hydroxylase for brain expression; globin, Immunoglobulin heavy and light chains for blood cell expression; and osteonectin, osteocalcin, osteopontin for bone expression.

The term "tissue-specific promoter" means that the promoter will allow transcription of RNA from the vector primarily only in a specific tissue in which the promoter is activated. For example, muscle cell specific promoters will only allow transcription in muscle cells. However, even with tissue-specific promoters some low level (about 10% or less than that observed in the desired tissue) expression might occur in other cell types. The promoter would still be defined as tissue-specific. Methods of achieving tissue-specific gene expression as set forth in International Publication No. WO 93/09236, filed Nov. 3, 1992 and published May 13, 1993; International Application No. PCT/US93/03993, filed Apr. 28, 1993; International Application No. PCT/US93/03985, filed Apr. 28, 1993; and U.S. patent application entitled "Specific Expression Vectors and Methods of Use", filed Nov. 1, 1993 and U.S. patent application entitled "Keratin K1 Expression Vectors and Methods of Use"; all (including drawings) are hereby incorporated by reference herein.

In preferred embodiments either the albumin enhancer/promoter, IE-CMV, RSV-LTR or DHFR promoters are used.

In one preferred embodiment the E1 and E2 or E1/E2 gene fusion sequences are a distance of at least about 1 Kb 5' and 3' from the origin of replication.

In another embodiment of the present invention the origin of replication may be selected from one type of papilloma virus, for example BPV-1, and the E1 gene sequence may be selected from the same papilloma virus or another papilloma virus, for example HPV, and the E2 gene sequence may be selected from the same type of papilloma virus as used for the origin of replication or for the E1 gene sequence or a different papilloma virus than one or both of the papilloma viruses from which the origin of replication and E1 gene sequence were selected from. Combinations of, or parts thereof, such as the origin of replication, E1 gene sequence and E2 gene sequence or E1/E2 gene fusion sequence, as set forth above, may be combined in a vector and assayed as is known in the art to determine functional combinations thereof.

Another embodiment of the present invention includes the use of an E1/E2 fusion gene. In this embodiment, to insure that both the E1 and E2 gene sequences are expressed the E1 and E2 gene sequences are linked by the use of internal ribosome entry sites from the encephalomyocarditis ("EMC") or polio virus in the production of polycistronic messages. By linking both the E1 and E2 gene sequences, both proteins would be encoded on a single mRNA species to insure production of both In this embodiment, only one ribonucleic acid species, translation of which will result in the production of two separate proteins, would be necessary to support maintenance of episomal replication. The fusion gene will contain at least the trans-activation region of the E2 protein.

In another embodiment of the invention a papilloma virus origin of replication and a first promoter transcriptionally linked to a therapeutic nucleic acid sequence are contained on a first episomal vector and a papilloma virus origin of replication, a second promoter transcriptionally linked to a papilloma virus E1 gene sequence and a third promoter transcriptionally linked to a papilloma virus E2 gene sequence are contained on a second episomal vector.

Alternatively, a papilloma virus origin of replication, a first promoter transcriptionally linked to a therapeutic nucleic acid sequence and either one of a second promoter transcriptionally linked to a papilloma virus E1 gene sequence or a third promoter transcriptionally linked to a papilloma virus E2 gene sequence are contained on a first episomal vector and a papilloma virus origin of replication, and the other one of a second promoter transcriptionally linked to a papilloma virus E1 gene sequence and a third promoter transcriptionally linked to a papilloma virus E2 gene sequence are contained on a second episomal vector.

Alternatively, a three vector system may be utilized, each vector containing a papilloma virus origin of replication, and one episomal vector containing a first promoter transcriptionally linked to a therapeutic nucleic acid sequence. A second episomal vector containing a second promoter transcriptionally linked to a papilloma virus E1 gene sequence.

A third episomal vector containing a third promoter transcriptionally linked to a papilloma virus E2 gene sequence.

In yet another embodiment, a papilloma virus origin of replication and a first promoter transcriptionally linked to a therapeutic nucleic acid sequence are contained on a first episomal vector and a second promoter transcriptionally linked to an E1/E2 fusion gene sequence, the fusion gene sequence containing at least the transactivation region of the E2 gene sequence, are contained on a second episomal vector. In all of the above multiple vector systems, the separate vectors are co-administered such that all species of vector are present in at least some of the same cells.

In another embodiment of the present invention there is provided a method of stably transforming a cell in a human or other animal cell which is accomplished by introducing the episomal vector into the cell. Once introduced into the cell, a stably transformed cell is made.

The term "stable transformation" as used herein refers to episomal transformation in which the introduced therapeutic nucleic acid sequence or sequences is not incorporated into the chromosomes of the whole cell, but rather is replicated as an extra-chromosomal element. This leads to a stable change or transformation of a given characteristic of a cell.

The term "transformed" as used herein refers to a process for making or introducing a stable change in the characteristics (express phenotype) of a cell by the mechanism of gene transfer whereby DNA or RNA is introduced into a cell in a form where it expresses a specific gene product or alters an expression of or affects endogenous gene products. In the present invention this process involves the introduction of the episomal vector into the cell. The episomal vector can be introduced into the cell by a variety of methods including microinjection, CaPO$_4$ precipitation, lipofection (liposome fusion), use of a gene gun and DNA vector transporter.

The term "DNA vector transporter" as used herein refers to those molecules which bind to the episomal vector system of the present invention and are capable of being taken up by cells. A DNA transporter is a molecular complex capable of non-covalent binding to the DNA of the episomal vector system and efficiently transporting the DNA through the cell membrane. Although not necessary, it is preferable that the transporter also transport the DNA through the nuclear membrane.

In another embodiment of the present invention there is provided the use of the episomal vector system for gene therapy treatment of uncontrolled cellular proliferative diseases, such as cancer. An episomal vector containing a nucleic acid sequence encoding a polypeptide which when expressed results in cell death is administered to a human or other animal.

Other and further objects, features and advantages will be apparent from the following description of the presently preferred embodiments of the invention which are given for the purpose of disclosure when taken in conjunction with the accompanying drawings.

Figure 1:
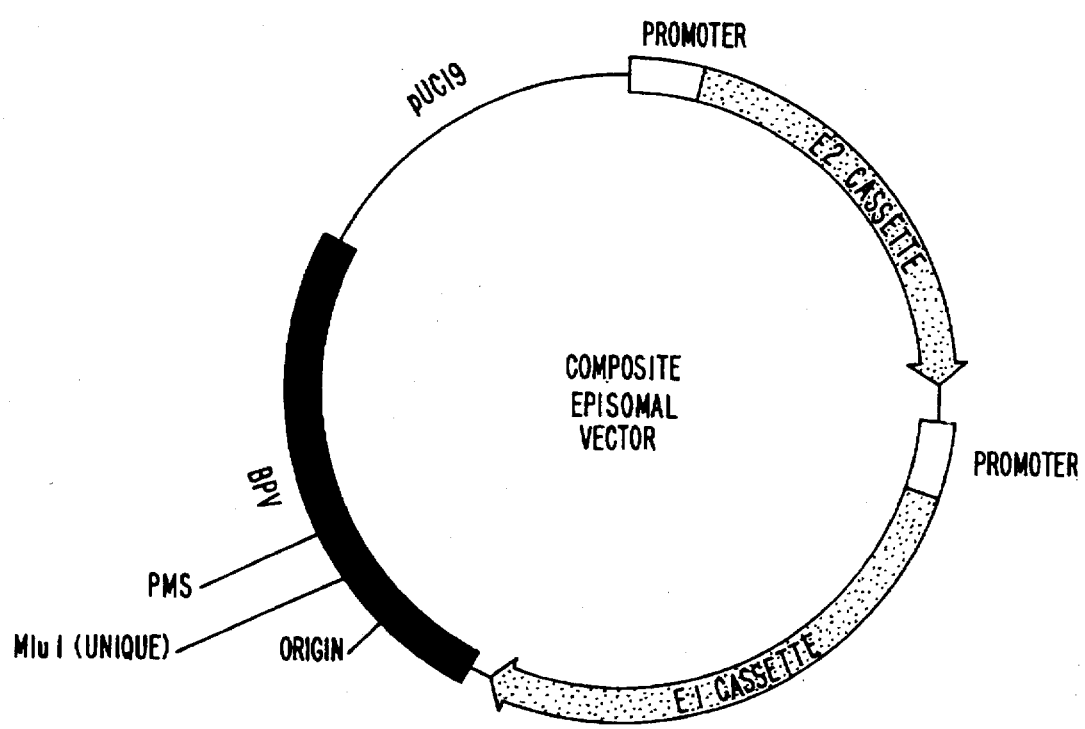
FIG. 1 shows a schematic representation of a BPV-1 episomal vector. The viral origin of replication (ORIGIN) and Vector Maintenance Sequence (VMS) locations are indicated within the BPV-1 polyfunctional nucleic acid sequence (nucleotides 4780 to 471 from the BPV-1 genome, 3636 bp). The Mlu I site is unique and is used to insert a therapeutic nucleic acid sequences or sequences. Insertions at this site do not interfere with viral replication.

The drawings are not necessarily to scale. Certain features of the invention may be exaggerated in scale or shown in schematic form in the interest of clarity and conciseness.

DETAILED DESCRIPTION OF THE INVENTION

A variety of eukaryotic expression vectors have been constructed from the BPV-1 genome utilizing the 69% region to drive episomal replication in C127I cells. These vectors have been used to study inducible elements as well as to synthesize a variety of compounds. All of these studies have been carried out in C127I or ID-13 cells (derived from C127I cells which contain multiple integrated copies of the BPV-1 genome and produce viral proteins.) It is known that the viral E1 and E2 proteins are necessary in conjunction with the origin of replication to support episomal replication of plasmids containing the origin.

When transfected into a variety of cell lines, including HeLa, CV-1 and 293, the plasmids containing an endogenous viral promoter to drive transcription of the viral open reading frames encoded in E1 and E2 and a viral origin do not replicate. However, when the immediate early cytomegalovirus (IECMV) promoter was used to drive the expression of E1 and E2, episomal replication was observed. The cell types used, however, are all epithelial or fibroblast-like and these are the cell types normally permissive for BPV-1 replication. It would be useful to have a vector for gene therapy which would replicate in a broad range of cell types and allow for expression of a therapeutic nucleic acid sequence or sequences contained in the vector.

Current approaches to gene therapy for, for example, liver diseases fall into two main categories with respect to overall mechanism and delivery—viral and non-viral. Non-viral methods of delivery such as receptor-mediated DNA delivery have been used to introduce DNA to the liver in vivo. Only transient expression has been observed from constructs targeted to the liver without prior partial hepatectomy. If a partial hepatectomy proceeds the introduction of the DNA/protein conjugate, the period of expression is extended, but not indefinitely.

The ability to achieve long-term expression of targeted DNAs in which the risks and costs of invasive surgical procedure such as partial hepatectomy are avoided is of great importance. The present invention utilizing an episomally replicating vector containing portions of a papilloma virus genome provides a solution to this problem. Particular regions of the BPV-1 genome can be stimulated in the quiescent liver or other tissues and can be stably maintained long-term when targeted to the liver or other organs by receptor-mediated DNA delivery.

One embodiment of the present invention includes an episomal vector system for gene therapy in humans or animals comprising a polyfunctional nucleic acid sequence of BPV-1 in a vector, the polyfunctional nucleic acid sequence including an origin of replication, a vector maintenance sequence a first promoter and a unique restriction site; for example, a unique Mlu I or other restriction enzyme site as are known in the art, for insertion of one or more therapeutic nucleic acid sequences; a first expression cassette containing the BPV-1 E1 gene sequence and a second promoter to drive transcription of the E1 genes; a second expression cassette containing the BPV-1 E2 gene sequence and a third promoter to drive transcription of the E2 gene; the first and second expression cassettes cloned into the vector and the episomal vector system includes one or more episomal vectors each, capable of episomal replication in a human or animal cell.

One skilled in the art recognizes that a variety of vectors will work. In FIG. 1 there is shown a schematic representation of the BPV-1 episomal vector using a pUC 19 plasmid. The "BPV-1 origin" region is approximately 1457 base pairs in length and includes a nucleotide sequence from 6959 to 7945/1 and 7945/1 to 470 of the BPV-1 genome.

The origin of replication and plasmid maintenance sequence locations are indicated within the BPV-1 polyfunctional nucleic acid sequence. The origin of replication corresponds to nucleotide 7945/1 of the BPV-1 genome. The minimal sequence for the BPV-1 origin of replication is defined by a 41 nucleotide sequence containing bases 7935 to 30.

In one embodiment a unique Mlu I site is used to insert a therapeutic nucleic acid sequence or sequences. Insertions at this site do not interfere with viral replication. In FIG. 1 there is also shown the E1 gene sequence and an E2 gene sequence with their promoters. The promoters can be identical or different. The location of the E1 and E2 gene sequences to the origin of replication is not important; except that they must be at least about 1 kb 5' and 3' from the origin of replication, otherwise they will interfere with replication of the episomal vector.

In a specific embodiment of the present invention the episomal vector mimics the arrangements of the E1 and E2 gene sequences relative to the replication origin found in the viral genome. The insertion of strong heterologous promoters in close proximity to the BPV-1 origin of replication interferes with replication. For this reason, promoters driving the expression of the E1 and E2 gene sequences are placed away from the viral origin to minimize this "squelching effect." In one example the E1 and E2 gene sequences are oriented in a head-to-tail arrangement of the basic layout of the episomal vector as depicted in FIG. 1. One skilled in the art recognizes that this is for example purposes and that a variety of other arrangements are readily determined. The vector is constructed to allow for the insertion of different promoter elements upstream of the E1 and E2 gene sequences. Unique cloning sites are also present at various sites in the construct to allow for the insertion of reporter and or therapeutic nucleic acid sequences.

One skilled in the art will readily recognize that the first, second and third promoters can be identical or different. They can be from ubiquitously expressed genes or from tissue-specific expressed genes. However, where the tissue-specific promoters are different, they must all be capable of providing expression in a specific tissue type. For example, three different liver specific promoters may be utilized. Examples of some promoters which have been found useful in the present invention include the promoter for ubiquitously expressed genes including phosphoglycerolkinase, IE-CMV, RSV-LTR or DHFR.

Tissue-specific promoters include insulin promoter for pancreatic expression, creatine kinase promoter for skeletal muscle expression, immunoglobulin heavy chain promoter/enhancer for B-cell expression, albumin enhancer/promoter, tyrosine aminotransferase promoter, transferrin promoter, cytochrome P-450 promoter, apolipoprotein E promoter, apolipoprotein A-1 promoter and β-actin promoter for liver expression, elastin, alpha-1 (I) collagen, keratin for skin expression; alpha actin, beta myosin heavy chain, myosin light chain, aldolase A for muscle expression; type 4 collagenase, Clara protein, serine dehydratase for lung expression; myelin basic protein, beta amyloid precursor protein, glutamine synthetase, tyrosine hydroxylase for brain expression; globin, Immunoglobulin heavy and light chains for blood cell expression; and osteonectin, osteocalcin, osteopontin for bone expression.

One skilled in the art readily recognizes that specific promoters can be used in brain, lung, bone, blood and other tissues.

An alternate approach to insure that both the E1 and E2 gene sequences are expressed is to make sure that both E1 and E2 are linked by the use of internal ribosome entry sites from the encephalomyocarditis ("EMC") or polio virus in the production of polycistronic messages. By linking both the E1 and E2 gene sequences, both proteins would be encoded on a single mRNA species to insure production of both.

One skilled in the art will readily recognize that the most important criteria used in the selection of a promoter to drive the expression of the E1 and E2 viral replication factors and the reporter gene nucleic acid sequences or therapeutic nucleic acid sequence or sequences is the ability of that promoter to drive long-term expression in the tissue of choice. Tissue specificity can be achieved at the level of delivery and promoters will not be eliminated as potential candidates should they be expressed in tissues other than the specific tissue of interest. Each therapy will have its own set of constraints with respect to the specificity of expression required and the level necessary for the treatment to have efficacy. In the preferred vectors, the primary objective is to achieve the highest sustained level of expression possible. Modulation of expression is undertaken when specific therapy requirements become apparent.

The long terminal repeat of the Rous Sarcoma Virus (RSV-LTR) is used in the preferred embodiment. The RSV-LTR promoter is capable of driving high levels of expression both in cultured episomal cells and in primary hepatocytes and a variety of other tissues. High level expression is seen in hepatocytes transduced both in vivo and in vitro. The LTR of Moloney Murine leukemic virus has also been used to drive expression in vivo.

In using the tissue-specific promoters, the albumin enhancer/promoter has been the preferred embodiment for liver cells. The albumin enhancer/promoter is a strong promoter relative to other promoters expressed in the liver. This promoter has been found to drive long-term expression in both primary hepatocytes and retrovirally transduced implanted hepatocytes. An additional advantage of this promoter is the tissue specificity of the albumin regulatory regions. Any leakiness in the delivery system will be less likely to drive transcription in any tissues other than the liver.

One skilled in the art readily recognizes the most efficient application of the papilloma virus episomal replication system in vivo requires that the E1 and E2 gene sequences and the therapeutic nucleic acid sequence or sequences, origin of replication and vector maintenance sequences are all contained in a single vector. The arrangement of these elements for optimum replication and maintenance will depend on the type of tissue being transformed, as well as the specific therapeutic nucleic acid sequence or sequences being used. In devising the optimization strategy for a vector construction, it is important to consider the location of the gene sequences relative to the origin, selection of the promoter, potential recombination between homologous sequences and the overall size of the vector as it pertains not so much to delivery but to replication efficiency. Within these constraints one skilled in the art will readily recognize how to optimize this arrangement for each specific use. The Hepa1A replication assay system described in Example 2 can be used to optimize the vectors for these criteria.

Administration

The episomal vector containing a particular therapeutic nucleic acid sequence or sequences can be administered prophylactically, or to patients having a disease or condition treatable by supplying and expressing a particular therapeutic nucleic acid sequence or sequences, e.g., by exogenous delivery of a naked episomal vector containing a therapeutic nucleic acid sequence or sequences, an episomal vector containing a therapeutic nucleic acid sequence associated with specific carriers, by means of an appropriate delivery vehicle, e.g., a liposome, by use of iontophoresis, electroporation and other pharmacologically approved methods of delivery. Routes of administration may include intramuscular, intravenous, aerosol, oral (tablet or pill form), topical, systemic, ocular, as a suppository, intraperitoneal and/or intrathecal.

The specific delivery route of an episomal vector containing a therapeutic nucleic acid sequence or sequences will depend on the use of the episomal vector.

Some methods of delivery that may be used include:
a. encapsulation in liposomes,
b. localization to nuclear compartment utilizing nuclear targeting site found on most nuclear proteins,
c. transfection of cells ex vivo with subsequent reimplantation or administration of the transfected cells,
d. a DNA transporter system.

At least three types of delivery strategies are useful in the present invention, including: Injection of naked episomal vector containing a therapeutic nucleic acid sequence or sequences, or injection of charge modified episomal vector containing a therapeutic nucleic acid sequence or sequences, or particle carrier drug delivery vehicles. Unmodified nucleic acid sequence encoding episomal vector containing a therapeutic nucleic acid sequence or sequences, like most small molecules, are taken up by cells, albeit slowly. To enhance cellular uptake, the episomal vector containing a therapeutic nucleic acid sequence or sequences may be modified in ways which reduce its charge but will maintain the expression of specific functional groups in the final translation product. This results in a molecule which is able to diffuse across the cell membrane, thus removing the permeability barrier.

Chemical modifications of the phosphate backbone will reduce the negative charge allowing free diffusion across the membrane. This principle has been successfully demonstrated for antisense DNA technology which shows that this is a feasible approach. In the body, maintenance of an external concentration will be necessary to drive the diffusion of the modified nucleic acid sequence encoding episomal vectors containing a therapeutic nucleic acid sequence or sequences into the cells of the tissue. Administration routes which allow the tissue to be exposed to a transient high concentration of the nucleic acid sequence encoding an episomal vector containing a therapeutic nucleic acid sequence or sequences, which is slowly dissipated by systemic adsorption are preferred. Intravenous administration with a drug carrier designed to increase the circulation half-life of the nucleic acid sequence encoding an episomal vector containing a therapeutic nucleic acid sequence or sequences can be used. The size and composition of the drug carrier restricts rapid clearance from the blood stream. The carrier, made to accumulate at the desired site of transfer, can protect the nucleic acid sequence encoding an episomal vector containing a therapeutic nucleic acid sequence or sequences from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for a nucleic acid sequence encoding an episomal vector containing a therapeutic nucleic acid sequence or sequences. These carriers have been developed for chemotherapeutic agents and protein-based pharmaceuticals, and consequently, can be adapted for nucleic acid delivery.

Chemical modification of the nucleic acid sequence encoding an episomal vector containing a therapeutic nucleic acid sequence or sequences to neutralize negative charge may be all that is required for penetration. However, in the event that charge neutralization is insufficient, the nucleic acid sequence encoding an episomal vector containing a therapeutic nucleic acid sequence receptor can be co-formulated with permeability enhancers, such as Azone or oleic acid, in a liposome. The liposomes can either represent a slow release presentation vehicle in which the modified nucleic acid sequence encoding an episomal vector containing a therapeutic nucleic acid sequence or sequences and permeability enhancer transfer from the liposome into the targeted cell, or the liposome phospholipids can participate directly with the modified nucleic acid sequence encoding an episomal vector containing a therapeutic nucleic acid sequence or sequences and permeability enhancer can participate directly thereby facilitating cellular delivery. In some cases, both the nucleic acid encoding an episomal vector containing a therapeutic nucleic acid sequence or sequences and permeability enhancer can be formulated into a suppository formulation for slow release.

The nucleic acid sequence encoding an episomal vector containing a therapeutic nucleic acid sequence or sequences may also be systemically administered. Systemic absorption refers to the accumulation of drugs in the blood stream followed by distribution throughout the entire body. Administration routes which lead to systemic absorption include: intravenous, intramuscular, subcutaneous, intraperitoneal, intranasal, intrathecal and ophthalmic. A gene gun may also be utilized. Administration of DNA-coated microprojectiles by a gene gun requires instrumentation but is as simple as direct injection of DNA. A construct bearing the gene of interest is precipitated onto the surface of microscopic metal beads. The microprojectiles are accelerated with a shock wave or expanding helium gas, and penetrate tissues to a depth of several cell layers. This approach permits the delivery of foreign genes to the skin of anesthetized animals. This method of administration achieves expression of transgenes at high levels for several days and at detectable levels for several weeks. Each of these administration routes exposes the nucleic acid sequence encoding an episomal vector containing a therapeutic nucleic acid sequence or sequences to an accessible targeted tissue. Subcutaneous administration drains into a localized lymph node which proceeds through the lymphatic network into the circulation. The rate of entry into the circulation has been shown to be a function of molecular weight or size. The use of a liposome or other drug carrier localizes the nucleic acid sequence encoding an episomal vector containing a therapeutic nucleic acid sequence at the lymph node. The nucleic acid sequence encoding an episomal vector containing a therapeutic nucleic acid sequence or sequences can be modified to diffuse into the cell, or the liposome can directly participate in the delivery of either the unmodified or modified nucleic acid sequence encoding an episomal vector containing a therapeutic nucleic acid sequence or sequences to the cell. Liposomes injected intravenously show accumulation in the liver, lung and spleen. The composition and size can be adjusted so that this accumulation represents 30% to 40% of the injected dose. The remaining dose circulates in the blood stream for up to 24 hours.

The chosen method of delivery should result in cytoplasmic accumulation and molecules should have some nuclease-resistance for optimal dosing. Nuclear delivery may also be used. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 1–1000 μg/kg of body weight/day. The duration of treatment will extend through the course of the disease symptoms, possibly continuously. The number of doses will depend upon disease delivery vehicle and efficacy data from clinical trials.

Another method of administration involves the use of a DNA transporter system for inserting specific DNA into a cell. The DNA transporter system comprises a plurality of a first DNA binding complex, the complex including a first binding molecule capable of non-covalently binding to DNA, the first binding molecule covalently linked to a surface ligand, the surface ligand capable of binding to a cell surface receptor; a plurality of a second DNA binding complex, the complex including a second binding molecule capable of non-covalently binding to DNA, the second binding molecule covalently linked to a nuclear ligand, the nuclear ligand capable of recognizing and transporting a transporter system through a nuclear membrane; wherein the plurality of first and second DNA binding complexes are capable of simultaneously, non-covalently binding to a specific DNA.

Additionally, a plurality of a third DNA binding complex may be used, the complex includes a third binding molecule capable of non-covalently binding to DNA, the third binding molecule covalently linked to a virus; wherein the plurality of third DNA binding complexes are capable of simultaneously, non-covalently binding to a specific DNA.

The first binding molecule, the second binding molecule and third binding molecule can each be selected from the group consisting of spermine, spermine derivative, histones, cationic peptides and polylysine. Spermine derivative refers to analogues and derivatives of spermine and include compounds as set forth in International Publication No. WO 93/18759, filed Mar. 19, 1993 and published Sep. 30, 1993, hereby incorporated by reference.

Establishment of therapeutic levels of nucleic acid sequence encoding an episomal vector containing a therapeutic nucleic acid sequence or sequences within the cell is dependent upon the rates of uptake and degradation. Decreasing the degree of degradation will prolong the intracellular half-life of the episomal vector containing a therapeutic nucleic acid sequence or sequences. Descriptions of useful systems are provided in the art cited above, all of which is hereby incorporated by reference.

An episomal vector containing a therapeutic nucleic acid sequence or sequences may be administered utilizing an ex vivo approach whereby cells are removed from an animal, transduced with the episomal vector containing a therapeutic nucleic acid sequence or sequences and reimplanted into the animal. The liver can be accessed by an ex vivo approach by removing hepatocytes from an animal, transducing the hepatocytes in vitro with the episomal vector containing a therapeutic nucleic acid sequence or sequences and reimplanting them into the animal (e.g., as described for rabbits by Chowdhury et al., Science 254:1802–1805, 1991, or in humans by Wilson, Hum. Gene Ther. 3:179–222, 1992) incorporated herein by reference.

The episomal vector containing a therapeutic nucleic acid sequence or sequences may be administered utilizing an in vivo approach whereby the gene will be administered directly to an animal by intravenous injection, intramuscular injection, or by catheterization and direct delivery of the gene via the blood vessels supplying the target organ.

The following examples are offered by way of illustration and are not intended to limit the invention in any manner.

EXAMPLE 1

Construction of an Episomal Vector

The parent plasmid for this construction is pUCPst which consists of pUC18 containing the BPV-1 sequence between bases 4780 and 471 bp (3636 bp). The origin of replication in this plasmid is located at base 7945/1. The unique sites in the multiple cloning region of pUCPst are used for the insertion of gene sequences for E1 and E2. IECMV promoter driven cassettes for E1 and E2 are obtained with EcoRI (5') to XhoI (3') digests of pCGEAG and pCGE2. The ends of these fragments are filled in with the Klenow fragment of DNA polymerase and linkers are added. The gene sequences are then cloned into the Hind III (E2) and Bam HI sites (E1), in a head to tail configuration as depicted in FIG. 1.

EXAMPLE 2

Replication Assay for use in the Episomal Cells

Figure 2:
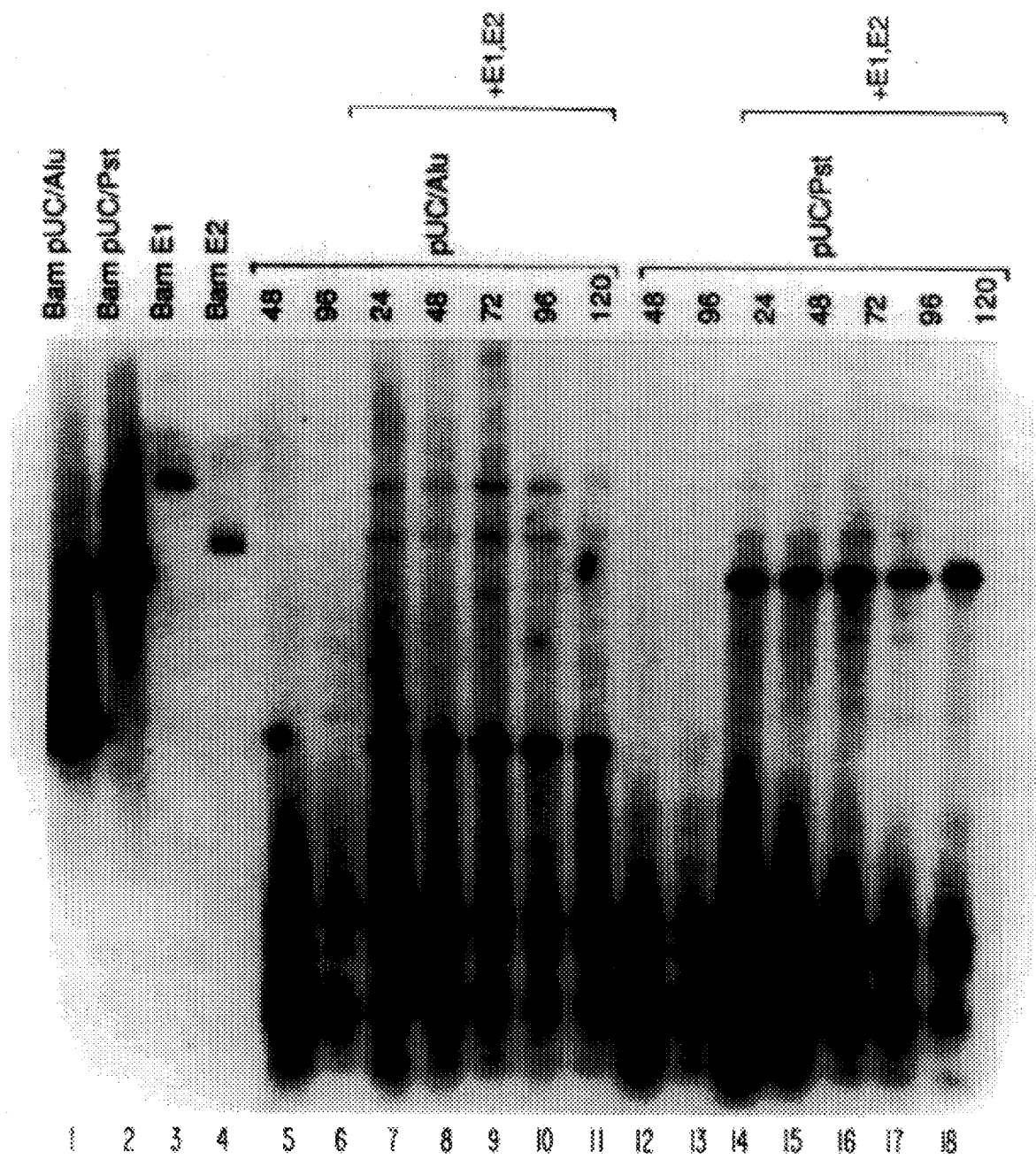
FIG. 2 shows replication of BPV-1 origin-containing plasmids in Hepa1A cells. A transient replication assay using the E1 and E2 expression vector in conjunction with the origin plasmid pUC/Alu (viral sequence 7890-52) or pUC/Pst (viral sequence 4780-471). 10 µg of the origin plasmid was transfected either alone or with 15 µg of both the E1 or E2 expression vectors. In each group, the final amount of DNA transfected was brought to 40 µg with the control plasmid pCMVβgal.

The method of Ustav and Stenlund, "Transient Replication of BPV-1 Requires Two Viral Polypeptides Encoded by the E1 and E2 Open Reading Frames" *EMBO J.* 10:449–457 (1991) is used for the replication assay in episomal cells. The origin plasmid designated pUC/Alu contains the viral sequences between 7890 and 52 (107 bp) in pUC19. The plasmid pUC/Pst contains a viral sequence between 4780 and 471 (3636 bp). The expression vectors for E1 and E2 are driven by the IECMV promoter. The cells ($10^7$) are mixed with a total of 40 µg of DNA and 500 µl of serum-containing media. Electroporation is then carried out in the Gene-Pulsar apparatus (Bio-Rad) with a 230-Volt, 960 µFd pulse. Cells are pelleted through 10 ml of serum-containing media and plated on 6×10 cm dishes. Extrachromosomal DNA is prepared at 24-hour time points and half of the recovered DNA was digested with BamHI and DpnI, electrophoresed on 0.8%, 1X TAE gels and Southern blotted. Filters were hybridized with pUC19 sequences generated by radioactive labelling with random primers. The results obtained from mouse hepatoma cell lines HepaIA are shown in FIG. 2. Time points in each set are 24, 48, 72, 96, and 120 hours.

Newly replicated material in mammalian cells was resistant to digestion by DpnI while residual bacterial plasmid DNAs were sensitive. The DpnI resistant material (replicated DNA) is linearized by BamHI and forms a 2793 bp band for replicated pUC/Alu (see Control Lane 1 and Lane 7–11), and a 6322 bp band for replicated pUC/Pst (see Control Lane 2 and Lanes 14–18). The DpnI sensitive material (unreplicated DNA) forms a series of lower molecular weight bands. Cells which receive the origin plasmid in the absence of the E1 and E2 expression vectors were completely devoid of any replicated material (see Lanes 5, 6, 12 and 13). This data indicates that both plasmids replicated in the presence of the viral E1 and E2 polypeptides. The amount of replicating material did not appear to increase significantly after 24 hours, but ori plasmids were maintained at steady state levels with time while the unreplicated input material was gradually lost.

EXAMPLE 3

Requirement of E1 and E2 to Support Episomal BPV-1 Replication

Figure 3:
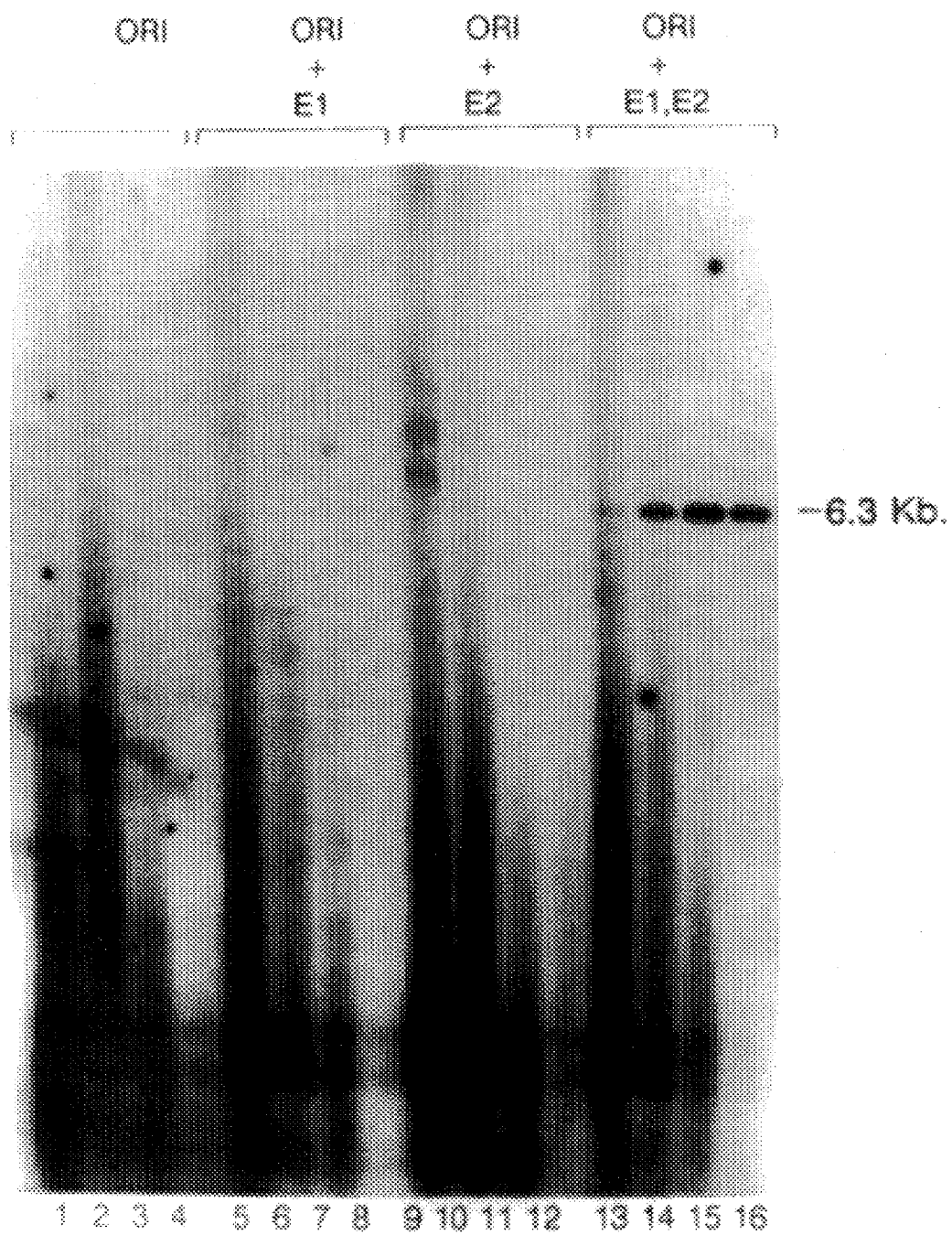
FIG. 3 shows replication of BPV-1 origin plasmid only in the presence of both E1 and E2. A transient replication assay using the E1 and E2 expression vectors as the only source, of viral trans replication factors. 10 µg of the origin plasmid pUC/Pst (viral sequence 4780-471) was transfected either alone or with 15 µg of one or both of the E1 or E2 expression vectors. In each group, the final amount of DNA transfected was brought to 40 µg with the control plasmid pCMVβgal.
Figure 4:
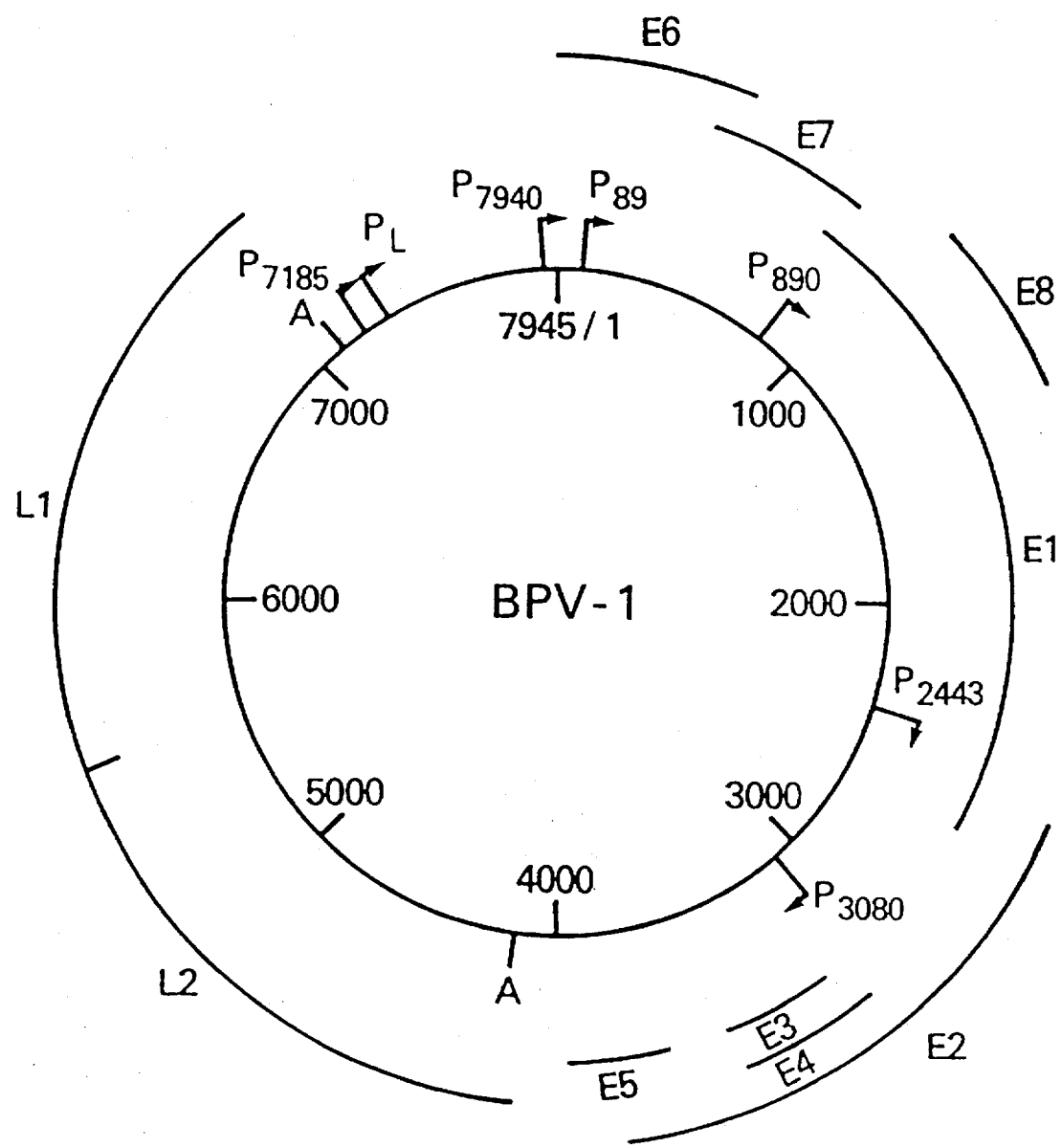
FIG. 4 shows a BPV-1 genomic map.

HepaIA cells are transfected in four sets. Each set contains 10 µg of larger ori plasmid pUC/Pst. The first set (FIG. 3, Lanes 1–4) contained the 30 µg of pCMVβgal in addition to the origin plasmid as control. The second set (FIG. 3, Lanes 5–8) contained 15 µg of pCMV-E1 and pCMVβgal. The third set contained 15 µg each of pCMV-E2 and pCMVβgal. The final set (FIG. 3, Lanes 9–12) contained 15 µg each of pCMV-E1 and pCMV-E2. The time points for each set are 24, 48, 72 and 96 hours post-transfection. Results demonstrate that there is an absolute requirement for E1 and E2 to support episomal BPV-1 replication in hepatoma cells. Similar results were also obtained in two human hepatoma cell lines, HepG2 and PLC. These results demonstrate that the viral origin-containing plasmids replicate episomally in a variety of cell types outside of epithelial and fibroblast lineages. Examples of other cell types which will support episomal vector replication include cells of endothelial, hematopoietic, muscle, nervous and glandular origin.

EXAMPLE 4

Measurement of E1 and E2

Cells are transfected as described previously and whole cell lysates made at various time points post-transfection. Samples are then subjected to RIA analysis with monoclonal antibodies. Bacterially expressed E1 and E2 peptides are used as the standards for this quantitative analysis.

EXAMPLE 5

Episomal Vectors in Primary Hepatocytes

Confluent cultures of primary hepatocytes are maintained in serum-free media for periods up to one month. Primary hepatocyte cultures are used for assessment of plasmid stability and copy number over a longer time frame than possible for proliferating hepatoma cells or C127I cells. Technically these cells closely approximate the in vivo condition of the quiescent liver with respect to transcription and replication. The rate of transfection of primary hepatocytes with lipofection is approximately 5% to 10%. To control for differences in transfection efficiencies between samples it is advantageous to lipofect a pool of cells. Twenty-four hours post-transfection the cells are trypsinized and split between a number of plates to be harvested and assayed at various time points (2–30 days post-transfection). Mouse hepatocytes are plated at a high density ($3-4 \times 10^6$ cells) in 150 mm dishes in 15 ml of hormonally defined, serum-deficient media. Approximately 20–40 µg of DNA in 150 µl of water is mixed with 150 µg of Lipofection (Gibco/BRL, Gaithersburg, Md.) in 150 µl water and added to cells for 16 hours in 5% $CO_2$ incubator maintained at 37° C. Media is aspirated and replaced. Twenty-four hours later cells are trypsinized and replated in multiple 6 cm dishes. At various time points post-transfection cells are harvested and replication assays performed as described in Example 2. In addition, the stability of the input DNA is determined. Long-term maintenance of the targeted DNA even in the absence of episomal replication can be important in achieving long-term expression.

When it is difficult to trypsinize and replate the cells after lipofection, parallel lipofections are carried out with the inclusion of pCMVβgal as an internal control to eliminate differences in transfection efficiencies. Immunoprecipitation is performed to determine the levels of E1 and E2 produced. The integrity of the plasmids are assayed by restriction mapping to determine the presence of rearrangements. Integrity of the vector after one month and a primary hepatocyte indicates potential stability when introduced to liver in vivo.

EXAMPLE 6

Production Assay BPV-1 Based Episomal Expression Vectors

The use of DNA/Protein complexes allows tissue-specific delivery of the DNA, by utilizing a protein that is recognized by a tissue-specific receptor. Hepatocytes contain a unique receptor which recognizes the galactose moiety of asialoglycoproteins (ASGP). Orosomucoid (OR) is a highly glycosylated serum protein which upon treatment with neuraminidase yields asialoorosomucoid (ASOR) (M. W. 40,000–60,000), and is cleared rapidly from circulation by the ASGP receptor. This liver specific receptor is present at approximately 500,000 receptors per hepatocyte. The large number of receptors greatly enhances the delivery capacity of DNA/Protein complexes to hepatocytes in the liver and as a result this type of delivery is very efficient in the expression of desired gene products in the liver.

The delivery of the episomal vector DNA by DNA/protein complexes to hepatocytes in vivo is used to achieve concentrations of E1 and E2 necessary to support episomal replication in mice. The amount of complex, in terms of DNA, injected varies depending upon the amount that gives maximum expression without side effects to the animal. In rats (200–250 grams) approximately 0.5–1 milligram of complex (based on DNA amount), in 0.15M saline, in a volume of 1000 µl, was injected into the tail vein. This resulted in 2–5 µg of DNA being injected per gram body weight, at a concentration of 0.5–1 µg/µl. Various amounts of complex, ranging from 0 to 500 µg (DNA based), in 0.15M saline, are injected at a concentration of 1 µg/µl into the tail vein in two groups of mice (8–10 weeks in age). Control animals are injected with the following at the same DNA concentrations; 1) a mixture of DNA and ASOR, 2) a mixture of DNA and poly-L-lysine, 3) 0.15M saline. The analysis of the DNA that has been delivered to the liver and the levels of E1 and E2 produced are measured. In addition, the replication status of the DNA present is determined with the use of DpnI digestion and Southern blotting. Two groups of duplicate C57/B6 mice are injected with the optimum amount of DNA, after which the animals are sacrificed at 0, 12, 24, 48, 72, and 96 hours post-injection. The livers are removed and the levels of replicated DNA is determined. The intensity of the hybridizing signal is compared to control DNA to estimate how much DNA is present and its half-life in the liver.

The levels of E1 and E2 are measured. A set of C57/B6 mice are injected with the maximal amount of DNA. The animals are sacrificed weekly during the first month and then monthly thereafter. The livers are removed, and the levels of the viral proteins are determined by RIA as described in Example 4.

EXAMPLE 7

Gene Therapy Treatment of Cancer

For the treatment of proliferative disease or cancer, the episomal vector of the present invention can be used. In the treatment, a therapeutic nucleic acid sequence or sequences is inserted into the episomal vector and a therapeutic dose is introduced into the animal or human to be treated. For example, thymidine kinase or another gene whose product results in cell death is delivered to the cancerous cells. A variety of delivery methods are available to those skilled in the art to specifically deliver the vector to the proliferative or cancer cells.

EXAMPLE 8

In vitro Production of a Therapeutic Gene Product Utilizing a Papilloma Virus

Episomal Vector

A specific cell line, for example a fibroblast or myoblast or hepatocyte or other cell line may be transformed with a papilloma virus episomal vector containing a therapeutic nucleic acid sequence or sequences. Expression of the therapeutic nucleic acid sequence or sequences will result in production of a polypeptide or polypeptides encoded by the therapeutic nucleic acid sequence or sequences. The polypeptide(s) may be harvested as is known in the art and utilized to treat a particular disease or condition. Alternatively, the harvested polypeptide(s) may be useful in an affinity chromatography column to bind and isolate a ligand. Additionally, the harvested polypeptide(s) may be used to raise antibodies, such as monoclonal antibodies, in a suitable animal. The episomal vector allows for the efficient and versatile production and isolation of a polypeptide for the above recited uses.

All patents and publications mentioned in this specification are indicative of the levels of those skilled in the art to which the invention pertains. All patents and publications are herein incorporated by reference to the same extent as if each individual publication is specifically and individually indicated to be incorporated by reference.

One skilled in the art will readily appreciate that the present invention is well adapted to carry out the objects and obtain the ends and advantages mentioned, as well as those inherent therein. The episomal vectors along with the methods, procedures, treatments, molecules, and specific compounds described herein are presently representative of preferred embodiments, are exemplary and are not intended as limitations on the scope of the invention. Changes therein and other uses will occur to those skilled in the art which are encompassed within the spirit of the invention and are defined by the scope within the claims.

What is claimed is:

1. An episomal vector system consisting essentially of:
   a papilloma virus origin of replication;
   a first promoter transcriptionally linked to a DNA sequence;
   a second promoter transcriptionally linked to a papilloma virus E1 gene sequence; and
   a third promoter transcriptionally linked to a papilloma virus E2 gene sequence; and
   wherein said second and third promoters and said E1 and E2 gene sequences are at least about 1 kb from said origin of replication, and said vector comprises no other papillomavirus coding sequences in addition to E1 and E2 gene sequences; and
   wherein said episomal vector system comprises one or more episomal vectors, each able to replicate as an episome.

2. The episomal vector system of claim 1 wherein said papilloma virus origin of replication and said first promoter transcriptionally linked to a DNA sequence are contained on a first episomal vector and said papilloma virus origin of replication, said second promoter transcriptionally linked to a papilloma virus E1 gene sequence and said third promoter transcriptionally linked to a papilloma virus E2 gene sequence are contained on a second episomal vector.

3. The episomal vector system of claim 1 wherein said papilloma virus origin of replication, said first promoter transcriptionally linked to a DNA sequence and either one of said second promoter transcriptionally linked to a papilloma virus E1 gene sequence or said third promoter transcriptionally linked to a papilloma virus E2 gene sequence are contained on a first episomal vector and said papilloma virus origin of replication, and the other one of said second promoter transcriptionally linked to a papilloma virus E1 gene sequence and said third promoter transcriptionally linked to a papilloma virus E2 gene sequence are contained on a second episomal vector.

4. The episomal vector system of claim 1, wherein said system consists of a single vector.

5. An episomal vector system consisting essentially of:
   a papilloma virus origin of replication;
   a vector maintenance sequence;
   a first promoter transcriptionally linked to a DNA sequence;
   a second promoter transcriptionally linked to an E1/E2 fusion gene sequence and no other papilloma virus coding sequences, said fusion gene sequence containing at least the trans-activation region of the E2 gene sequence; and
   wherein said second promoter and said E1/E2 fusion gene sequence is at least about 1 kb from said origin of replication; and
   wherein said episomal vector system comprises one or more episomal vectors, each able to replicate as an episome.

6. The episomal vector system of claim 5, wherein said system consists of a single vector.

7. The episomal vector system of claim 5 wherein said papilloma virus origin of replication and said first promoter transcriptionally linked to a DNA sequence are contained on a first episomal vector and said second promoter transcriptionally linked to an E1/E2 fusion gene sequence, said fusion gene sequence containing at least the trans-activation region of the E2 gene sequence, are contained on a second episomal vector.

8. The episomal vector system of claim 1–6, wherein said second promoter and said third promoter comprise an administered-compound-regulatable promoter wherein episomal replication occurs upon administration of a compound which interacts with said administered-compound-regulatable promoter and ceases upon cessation of administration of said compound.

9. The episomal vector system of claim 8 wherein said administered-compound-regulatable promoter transcriptionally linked to a nucleic acid is a steroid regulatable promoter and is activated by administration of a steroid hormone or steroid hormone analog.

10. The episomal vector system of claims 1–6 wherein said origin of replication, said vector maintenance sequence, said E1 sequence or said E2 sequence is from a Human papilloma virus.

11. The episomal vector system of claims 5–7 wherein said E1/E2 fusion gene sequence is a Human papilloma virus E1/E2 fusion gene sequence.

12. The episomal vector system of claims 1–6 wherein said origin of replication, said vector maintenance sequence, said E1 sequence or said E2 sequence is from a bovine papilloma virus.

13. The episomal vector system of claims 5–7 wherein said E1/E2 fusion gene sequence is a bovine papilloma virus E1/E2 fusion gene sequence.

14. The episomal vector system of claims 1–4 wherein said origin of replication, said E1 gene sequence and said E2 gene sequence are from a Human papilloma virus.

15. The episomal vector system of claims 1–4 wherein said origin of replication, said E1 gene sequence and said E2 gene sequence are from BPV-1.

16. The episomal vector system one of claims 5–7 wherein said origin of replication, and said E1/E2 fusion gene sequence are from BPV-1.

17. The episomal vector system of claims 1–4 wherein said origin of replication is selected from one type of papilloma virus, and said E1 gene is selected from the same type papilloma virus or another type papilloma virus, and said E2 gene is selected from the same type of papilloma virus as said origin of replication and for said E1 gene or a different type papilloma virus than one or both of the papilloma viruses from which said origin of replication and said E1 gene were selected.

18. The episomal vector system of claims 1–4 wherein said origin of replication is selected from one type of papilloma virus, and said E1 gene is selected from the same type papilloma virus or another type papilloma virus, and said E2 gene is selected from the same type of papilloma virus as said origin of replication or for said E1 gene or a different type papilloma virus than one or both of the papilloma viruses from which said origin of replication and said E1 gene were selected.

19. The episomal vector system of claims 5–7 wherein said origin of replication is selected from one type of papilloma virus, and said E1 gene sequence encoding the E1 portion of said E1/E2 fusion gene sequence is selected from the same type papilloma virus or another type papilloma virus, and said E2 gene sequence encoding the E2 portion of said E1/E2 fusion gene sequence is selected from the same type of papilloma virus as said origin of replication or for said E1 gene sequence or a different type papilloma virus than one or both of the papilloma viruses from which said origin of replication and said E1 gene sequence were selected.

20. The episomal vector system of claims 1–4 wherein one or more of said first, second and third promoters confer tissue-specific expression.

21. The episomal vector system of claim 20, wherein said promoters are tissue-specific promoters selected from the group consisting of:

insulin promoter for pancreatic expression;

creatine kinase promoter for skeletal muscle expression;

immunoglobulin heavy chain promoter/enhancer for B-cell expression;

albumin enhancer/promoter, tyrosine amino transferrin promoter, cytochrome P-450 promoter, apolipoprotein E promoter, apolipoprotein A-1 promoter and β-actin promoter for liver expression;

elastin, alpha-1 (I) collagen, keratin K1, K6 and loricrin for skin expression;

alpha actin, beta myosin heavy chain, myosin light chain, aldolase A for muscle expression;

type 4 collagenase, Clara protein, serine dehydratase for lung expression;

myelin basic protein, beta amyloid precursor protein, glutamine synthetase, tyrosine hydroxylase for brain expression;

globin, Immunoglobulin heavy and light chains for blood cell expression; and osteonectin, osteocalcin, osteopontin for bone expression.

22. The episomal vector system of claims 15 or 16 wherein said origin of replication is contained within a DNA sequence of about 3636 base pairs in length, and includes a nucleic acid sequence from Bovine papilloma virus type 1 from about nucleotide 6959 to 7945/1 and 7945/1 to about 471, wherein said Bovine papilloma virus type 1 nucleotide 7945/1 is within said origin of replication sequence of Bovine papilloma virus type 1.

23. The episomal vector system of claims 1–4 wherein both said second and third promoters are the same.

24. The episomal vector system of claim 23, wherein said promoters are an RSV-LTR.

25. The episomal vector system of claims 1–4 wherein said E1 and E2 gene sequences are a distance of at least about 1 Kb 5' and 3' from said origin of replication.

26. The episomal vector system of claims 5–7 wherein said E1/E2 fusion gene sequence is a distance of at least about 1 Kb 5' and 3' from said origin of replication.

27. The episomal vector system of claims 1–4 wherein said second and third promoters are albumin enhancer/promoters.

28. A method of producing a protein in vitro comprising the steps of introducing an episomal vector of claims 1–6 into a mammalian cell and expressing said DNA sequence such that production of said protein is detected.

29. The method of claim 28 wherein said DNA sequence is selected from the group consisting of nucleic acid sequences encoding enzymes, ligands, regulatory factors, and structural proteins.

30. The method of claim 28 wherein said DNA sequence is selected from the group consisting of nucleic acid sequences encoding nuclear proteins, cytoplasmic proteins mitochondrial proteins, secreted proteins, plasmallema-associated proteins, serum proteins, viral antigens, bacterial antigens, protozoal antigens and parasitic antigens.

31. The method of claim 28 wherein said DNA sequence is selected from the group consisting of nucleic acid sequences encoding proteins, lipoproteins, glycoproteins, phosphoproteins and nucleic acid.

32. The method of claim 28 wherein said DNA sequence is selected from the group consisting of nucleic acid sequences encoding hormones, growth factors, angiogenesis factors, matrix factors, enzymes, clotting factors, apolipoproteins, receptors, drugs, oncogenes, tumor antigens, tumor suppressors, viral antigens, parasitic antigens and bacterial antigens.

33. The method of claim 28 wherein the DNA sequence is selected from the group consisting of nucleic acid sequences encoding proinsulin, insulin, growth hormone, androgen receptors, insulin-like growth factor I, insulin-like growth factor II, insulin-like growth factor binding proteins, epidermal growth factor TGF-α, TGF-β, PDGF, acidic fibroblast growth factor, basic fibroblast growth factor, angiogenin, Type IV collagen, Type VII collagen, laminin, phenylalanine hydroxylase, tyrosine hydroxylase, ras, fos, myc, erb, src, sis, jun, E6 transforming sequence, E7 transforming sequence, p53 protein Rb gene product, cytokine receptor, IL-1, IL-6, IL-8 and viral capsid protein.

34. A method for stably transforming a mammalian cell in vitro comprising the steps of introducing an episomal vector of claims 1–4 into said mammalian cell and expressing said E1 and E2 genes.

35. A method for stably transforming a mammalian cell in vitro comprising the steps of introducing an episomal vector of claims 5 or 6 into said mammalian cell and expression of said E1 and E2 genes.

36. A method for stably transforming a mammalian cell in vitro comprising the steps of introducing an episomal vector as in claim 7 into said mammalian cell and expression of said E1 and E2 genes.

37. A method for the in vitro regulation of an episomal vector replication comprising the steps of introducing to a mammalian cell an episomal vector of claim 8 and administering or ceasing to administer a compound which interacts with said administered-compound-regulatable promoter, wherein said E1 and E2 genes are expressed or ceases to be expressed.

38. A method causing cessation of production of a protein in vitro, comprising introducing to a mammalian cell an episomal vector of claim 1–6 wherein said DNA sequence encodes a protein which causes cell death thereby inhibiting production of said protein.

39. The method of claim 38, wherein said protein which causes cell death is thymidine kinase.

* * * * *

UNITED STATES PATENT AND TRADEMARK OFFICE
CERTIFICATE OF CORRECTION

PATENT NO. : 5,674,703
DATED : October 7, 1997
INVENTOR(S) : Savio L.C. Woo, et al It is certified that error appears in the above-indentified patent and that said Letters Patent is hereby corrected as shown below:

On the title page, under item [56],

OTHER PUBLICATIONS, 2ND COLUMN; Sarver: Delete "Vectro" and insert --Vector--

Column 4, Line 1: After "proteins" insert --,--

Column 4, Line 20: Delete "phenylalaninehydroxylase" and insert --phenylalanine hydroxylase"

Column 4, Line 21: Delete "tyrosinehydroxylase" and insert --tyrosine hydroxylase--

Column 4, Line 64: Delete "asteroid" and insert --a steroid--

Column 4, Line 65: Delete "asteroid" and insert --a steroid--

Column 6, Line 37: Insert --.-- after "both"

Column 7, Line 64: Delete "acid sequences" and insert --acid sequence--

Column 8, Line 10: Delete "source," and insert --source--

UNITED STATES PATENT AND TRADEMARK OFFICE
CERTIFICATE OF CORRECTION

PATENT NO. : 5,674,703
DATED : October 7, 1997
INVENTOR(S) : Savio L.C. Woo, et al It is certified that error appears in the above-indentified patent and that said Letters Patent is hereby corrected as shown below:

Column 18, Line 15: After "Virus" insert --Episomal Vector--

Column 18, Line 16: Delete "Episomal Vector"

Column 29, Line 1: After "proteins" insert --,--

Column 29, line 26: After "protein" insert --,--

Signed and Sealed this

Twenty-third Day of June, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 3637
        ( B ) TYPE: nucleic acid -continued ( C ) STRANDEDNESS: single
( D ) TOPOLOGY: linear ( i i ) SEQUENCE DESCRIPTION: SEQ ID NO: 1:

| | | | | | |
|---|---|---|---|---|---|
| CTGCAGCTGC | AATCGTCCAT | TGCAGAAACA | TCTGGTTTAG | AAAATATTTT | 50 |
| TGTAGGAGGC | TCGGGTTTAG | GGGATACAGG | AGGAGAAAAC | ATTGAACTGA | 100 |
| CATACTTCGG | GTCCCCACGA | ACAAGCACGC | CCCGCAGTAT | TGCCTCTAAA | 150 |
| TCACGTGGCA | TTTTAAACTG | GTTCAGTAAA | CGGTACTACA | CACAGGTGCC | 200 |
| CACGGAAGAT | CCTGAAGTGT | TTTCATCCCA | AACATTTGCA | AACCCACTGT | 250 |
| ATGAAGCAGA | ACCAGCTGTG | CTTAAGGGAC | CTAGTGGACG | TGTTGGACTC | 300 |
| AGTCAGGTTT | ATAAACCTGA | TACACTTACA | ACACGTAGCG | GGACAGAGGT | 350 |
| GGGACCACAG | CTACATGTCA | GGTACTCATT | GAGTACTATA | CATGAAGATG | 400 |
| TAGAAGCAAT | CCCCTACACA | GTTGATGAAA | ATACACAGGG | ACTTGCATTC | 450 |
| GTACCCTTGC | ATGAAGAGCA | AGCAGGTTTT | GAGGAGATAG | AATTAGATGA | 500 |
| TTTTAGTGAG | ACACATAGAC | TGCTACCTCA | GAACACCTCT | TCTACACCTG | 550 |
| TTGGTAGTGG | TGTACGAAGA | AGCCTCATTC | CAACTCAGGA | ATTTAGTGCA | 600 |
| ACACGGCCTA | CAGGTGTTGT | AACCTATGGC | TCACCTGACA | CTTACTCTGC | 650 |
| TAGCCCAGTT | ACTGACCCTG | ATTCTACCTC | TCCTAGTCTA | GTTATCGATG | 700 |
| ACACTACTAC | TACACCAATC | ATTATAATTG | ATGGGCACAC | AGTTGATTTG | 750 |
| TACAGCAGTA | ACTACACCTT | GCATCCCTCC | TTGTTGAGGA | AACGAAAAAA | 800 |
| ACGGAAACAT | GCCTAATTTT | TTTTGCAGAT | GGCGTTGTGG | CAACAAGGCC | 850 |
| AGAAGCTGTA | TCTCCCTCCA | ACCCCTGTAA | GCAAGGTGCT | TTGCAGTGAA | 900 |
| ACCTATGTGC | AAAGAAAAAG | CATTTTTTAT | CATGCAGAAA | CGGAGCGCCT | 950 |
| GCTAACTATA | GGACATCCAT | ATTACCCAGT | GTCTATCGGG | GCCAAAACTG | 1000 |
| TTCCTAAGGT | CTCTGCAAAT | CAGTATAGGG | TATTTAAAAT | ACAACTACCT | 1050 |
| GATCCCAATC | AATTTGCACT | ACCTGACAGG | ACTGTTCACA | ACCCAAGTAA | 1100 |
| AGAGCGGCTG | GTGTGGGCAG | TCATAGGTGT | GCAGGTGTCC | AGAGGGCAGC | 1150 |
| CTCTTGGAGG | TACTGTAACT | GGGCACCCCA | CTTTTAATGC | TTTGCTTGAT | 1200 |
| GCAGAAAATG | TGAATAGAAA | AGTCACCACC | CAAACAACAG | ATGACAGGAA | 1250 |
| ACAAACAGGC | CTAGATGCTA | AGCAACAACA | GATTCTGTTG | CTAGGCTGTA | 1300 |
| CCCCTGCTGA | AGGGGAATAT | TGGACAACAG | CCCGTCCATG | TGTTACTGAT | 1350 |
| CGTCTAGAAA | ATGGCGCCTG | CCCTCCTCTT | GAATTAAAAA | ACAAGCACAT | 1400 |
| AGAAGATGGG | GATATGATGG | AAATTGGGTT | TGGTGCAGCC | AACTTCAAAG | 1450 |
| AAATTAATGC | AAGTAAATCA | GATCTACCTC | TTGACATTCA | AAATGAGATC | 1500 |
| TGCTTGTACC | CAGACTACCT | CAAAATGGCT | GAGGACGCTG | CTGGTAATAG | 1550 |
| CATGTTCTTT | TTTGCAAGGA | AAGAACAGGT | GTATGTTAGA | CACATCTGGA | 1600 |
| CCAGAGGGGG | CTCGGAGAAA | GAAGCCCCTA | CCACAGATTT | TTATTTAAAG | 1650 |
| AATAATAAAG | GGGATGCCAC | CCTTAAAATA | CCCAGTGTGC | ATTTTGGTAG | 1700 |
| TCCCAGTGGC | TCACTAGTCT | CAACTGATAA | TCAAATTTTT | AATCGGCCCT | 1750 |
| ACTGGCTATT | CCGTGCCCAG | GGCATGAACA | ATGGAATTGC | ATGGAATAAT | 1800 |
| TTATTGTTTT | TAACAGTGGG | GGACAATACA | CGTGGTACTA | ATCTTACCAT | 1850 |
| AAGTGTAGCC | TCAGATGGAA | CCCCACTAAC | AGAGTATGAT | AGCTCAAAAT | 1900 |

-continued

| | | | | | |
|---|---|---|---|---|---|
| TCAATGTATA | CCATAGACAT | ATGGAAGAAT | ATAAGCTAGC | CTTTATATTA | 1950 |
| GAGCTATGCT | CTGTGGAAAT | CACAGCTCAA | ACTGTGTCAC | ATCTGCAAGG | 2000 |
| ACTTATGCCC | TCTGTGCTTG | AAAATTGGGA | AATAGGTGTG | CAGCCTCCTA | 2050 |
| CCTCATCGAT | ATTAGAGGAC | ACCTATCGCT | ATATAGAGTC | TCCTGCAACT | 2100 |
| AAATGTGCAA | GCAATGTAAT | TCCTGCAAAA | GAAGACCCTT | ATGCAGGGTT | 2150 |
| TAAGTTTTGG | AACATAGATC | TTAAAGAAAA | GCTTCTTTG | GACTTAGATC | 2200 |
| AATTTCCCTT | GGGAAGAAGA | TTTTTAGCAC | AGCAAGGGGC | AGGATGTTCA | 2250 |
| ACTGTGAGAA | AACGAAGAAT | TAGCCAAAAA | ACTTCCAGTA | AGCCTGCAAA | 2300 |
| AAAAAAAAAA | AAATAAAAGC | TAAGTTTCTA | TAAATGTTCT | GTAAATGTAA | 2350 |
| AACAGAAGGT | AAGTCAACTG | CACCTAATAA | AAATCACTTA | ATAGCAATGT | 2400 |
| GCTGTGTCAG | TTGTTTATTG | GAACCACACC | CGGTACACAT | CCTGTCCAGC | 2450 |
| ATTTGCAGTG | CGTGCATTGA | ATTATTGTGC | TGGCTAGACT | TCATGGCGCC | 2500 |
| TGGCACCGAA | TCCTGCCTTC | TCAGCGAAAA | TGAATAATTG | CTTTGTTGGC | 2550 |
| AAGAAACTAA | GCATCAATGG | GACGCGTGCA | AAGCACCGGC | GGCGGTAGAT | 2600 |
| GCGGGGTAAG | TACTGAATTT | TAATTCGACC | TATCCCGGTA | AAGCGAAAGC | 2650 |
| GACACGCTTT | TTTTTCACAC | ATAGCGGGAC | CGAACACGTT | ATAAGTATCG | 2700 |
| ATTAGGTCTA | TTTTTGTCTC | TCTGTCGGAA | CCAGAACTGG | TAAAAGTTTC | 2750 |
| CATTGCGTCT | GGGCTTGTCT | ATCATTGCGT | CTCTATGGTT | TTTGGAGGAT | 2800 |
| TAGACGGGGC | CACCAGTAAT | GGTGCATAGC | GGATGTCTGT | ACCGCCATCG | 2850 |
| GTGCACCGAT | ATAGGTTTGG | GGCTCCCCAA | GGGACTGCTG | GGATGACAGC | 2900 |
| TTCATATTAT | ATTGAATGGG | CGCATAATCA | GCTTAATTGG | TGAGGACAAG | 2950 |
| CTACAAGTTG | TAACCTGATC | TCCACAAAGT | ACGTTGCCGG | TCGGGGTCAA | 3000 |
| ACCGTCTTCG | GTGCTCGAAA | CCGCCTTAAA | CTACAGACAG | GTCCCAGCCA | 3050 |
| AGTAGGCGGA | TCAAAACCTC | AAAAAGGCGG | GAGCCAATCA | AAATGCAGCA | 3100 |
| TTATATTTTA | AGCTCACCGA | AACCGGTAAG | TAAAGACTAT | GTATTTTTTC | 3150 |
| CCAGTGAATA | ATTGTTGTTA | ACAATAATCA | CACCATCACC | GTTTTTTCAA | 3200 |
| GCGGAAAAA | ATAGCCAGCT | AACTATAAAA | AGCTGCTGAC | AGACCCCGGT | 3250 |
| TTTCACATGG | ACCTGAAACC | TTTTGCAAGA | ACCAATCCAT | TCTCAGGGTT | 3300 |
| GGATTGTCTG | TGGTGCAGAG | AGCCTCTTAC | AGAAGTTGAT | GCTTTTAGGT | 3350 |
| GCATGGTCAA | AGACTTTCAT | GTTGTAATTC | GGGAAGGCTG | TAGATATGGT | 3400 |
| GCATGTACCA | TTTGTCTTGA | AAACTGTTTA | GCTACTGAAA | GAAGACTTTG | 3450 |
| GCAAGGTGTT | CCAGTAACAG | GTGAGGAAGC | TGAATTATTG | CATGGCAAAA | 3500 |
| CACTTGATAG | GCTTTGCATA | AGATGCTGCT | ACTGTGGGGG | CAAACTAACA | 3550 |
| AAAAATGAAA | AACATCGGCA | TGTGCTTTTT | AATGAGCCTT | TCTGCAAAAC | 3600 |
| CAGAGCTAAC | ATAATTAGAG | GACGCTGCTA | CGACTGC | | 3637 |

( 2 ) INFORMATION FOR SEQ ID NO: 2:

( i ) SEQUENCE CHARACTERISTICS:
( A ) LENGTH: 1451
( B ) TYPE: nucleic acid
( C ) STRANDEDNESS: single
( D ) TOPOLOGY: linear ( i i ) SEQUENCE DESCRIPTION: SEQ ID NO: 2:

| | | | | | |
|---|---|---|---|---|---|
| ACCTCTTGTG | TCCACGTTGT | GAATCTCGCG | AGCGTCATGG | CAAACGATAA | 50 |
| AGGTAGCAAT | TGGGATTCGG | GCTTGGGATG | CTCATATCTG | CTGACTGAGG | 100 |
| CAGAATGTGA | AAGTGACAAA | GAGAATGAGG | AACCCGGGGC | AGGTGTAGAA | 150 |
| CTGTCTGTGG | AATCTGATCG | GTATGATAGC | CAGGATGAGG | ATTTGTTGA | 200 |
| CAATGCATCA | GTCTTTCAGG | GAAATCACCT | GGAGGTCTTC | CAGGCATTAG | 250 |
| AGAAAAGGC | GGGTGAGGAG | CAGATTTTAA | ATTTGAAAAG | AAAAGTATTG | 300 |
| GGGAGTTCGC | AAAACAGCAG | CGGTTCCGAA | GCATCTGAAA | CTCCAGTTAA | 350 |
| AAGACGGAAA | TCAGGAGCAA | AGCGAAGATT | ATTTGCTGAA | AANGAAGCTA | 400 |
| ACCGTGTTCT | TACGCCCCTC | CAGGTACAGG | GGGAGGGGGA | GGGGAGGCAA | 450 |
| GAACTTAATG | AGGAGCAGGC | AATTAGTCAT | CTACATCTGC | AGCTTGTTAA | 500 |
| ATCTAAAAAT | GCTACAGTTT | TTAAGCTGGG | GCTCTTTAAA | TCTTTGTTCC | 550 |
| TTTGTAGCTT | CCATGATATT | ACGAGGTTGT | TTAAGAATGA | TAAGACCACT | 600 |
| AATCAGCAAT | GGGTGCTGGC | TGTGTTTGGC | CTTGCAGAGG | TGTTTTTTGA | 650 |
| GGCGAGTTTC | GAACTCCTAA | AGAAGCAGTG | TAGTTTTCTG | CAGATGCAAA | 700 |
| AAAGATCTCA | TGAAGGAGGA | ACTTGTGCAG | TTTACTTAAT | CTGCTTTAAC | 750 |
| ACAGCTAAAA | GCAGAGAAAC | AGTCCGGAAT | CTGATGGCAA | ACACGCTAAA | 800 |
| TGTAAGAGAA | GAGTGTTTGA | TGCTGCAGCC | AGCTAAAATT | CGAGGACTCA | 850 |
| GCGCAGCTCT | ATTCTGGTTT | AAAAGTAGTT | TGTCACCCGC | TACACTTAAA | 900 |
| CATGGTGCTT | TACCTGAGTG | GATACGGGCG | CAAACTACTC | TGAACGAGAG | 950 |
| CTTGCAGACC | GAGAAATTCG | ACTTCGGAAC | TATGGTGCAA | TGGGCCTATG | 1000 |
| ATCACAAATA | TGCTGAGGAG | TCTAAAATAG | CCTATGAATA | TGCTTTGGCT | 1050 |
| GCAGGATCTG | ATAGCAATGC | ACGGGCTTTT | TTAGCAACTA | ACAGCCAAGC | 1100 |
| TAAGCATGTG | AAGGACTGTG | CAACTATGGT | AAGACACTAT | CTAAGAGCTG | 1150 |
| AAACACAAGC | ATTAAGCATG | CCTGCATATA | TTAAAGCTAG | GTGCAAGCTG | 1200 |
| GCAACTGGGG | AAGGAAGCTG | GAAGTCTATC | CTAACTTTTT | TTAACTATCA | 1250 |
| GAATATTGAA | TTAATTACCT | TTATTAATGC | TTTAAAGCTC | TGGCTAAAAG | 1300 |
| GAATTCCAAA | AAAAAACTGT | TTAGCATTTA | TTGGCCCTCC | AAACACAGGC | 1350 |
| AAGTCTATGC | TCTGCAACTC | ATTAATTCAT | TTTTGGGTG | GTAGTGTTTT | 1400 |
| ATCTTTTGCC | AACCATAAAA | GTCACTTTTG | GCTTGCTTCC | CTAGCAGATA | 1450 |
| C | | | | | 1451 |

( 2 ) INFORMATION FOR SEQ ID NO: 3:

( i ) SEQUENCE CHARACTERISTICS:
        ( A ) LENGTH: 1257
        ( B ) TYPE: nucleic acid
        ( C ) STRANDEDNESS: single
        ( D ) TOPOLOGY: linear ( i i ) SEQUENCE DESCRIPTION: SEQ ID NO: 3:

| | | | | | |
|---|---|---|---|---|---|
| TTGACGAGGA | GGAGGATAGT | GAAGAGGATG | GAGACAGCAT | GCGAACGTTT | 50 |
| ACATGTAGCG | CAAGAAACAC | AAATGCAGTT | GATTGAGAAA | AGTAGTGATA | 100 |
| AGTTGCAAGA | TCATATACTG | TACTGGACTG | CTGTTAGAAC | TGAGAACACA | 150 |
| CTGCTTTATG | CTGCAAGGAA | AAAAGGGGTG | ACTGTCCTAG | GACACTGCAG | 200 |

```
AGTACCACAC  TCTGTAGTTT  GTCAAGAGAG  AGCCAAGCAG  GCCATTGAAA      250

TGCAGTTGTC  TTTGCAGGAG  TTAAGCAAAA  CTGAGTTTGG  GGATGAACCA      300

TGGTCTTTGC  TTGACACAAG  CTGGGACCGA  TATATGTCAG  AACCTAAACG      350

GTGCTTTAAG  AAAGGCGCCA  GGGTGGTAGA  GGTGGAGTTT  GATGGAAATG      400

CAAGCAATAC  AAACTGGTAC  ACTGTCTACA  GCAATTTGTA  CATGCGCACA      450

GAGGACGGCT  GGCAGCTTGC  GAAGGCTGGG  GCTGACGGAA  CTGGGCTCTA      500

CTACTGCACC  ATGGCCGGTG  CTGGACGCAT  TTACTATTCT  CGCTTTGGTG      550

ACGAGGCAGC  CAGATTTAGT  ACAACAGGGC  ATTACTCTGT  AAGAGATCAG      600

GACAGAGTGT  ATGCTGGTGT  CTCATCCACC  TCTTCTGATT  TTAGAGATCG      650

CCCAGACGGA  GTCTGGGTCG  CATCCGAAGG  ACCTGAAGGA  GACCCTGCAG      700

GAAAAGAAGC  CGAGCCAGCC  CAGCCTGTCT  CTTCTTTGCT  CGGCTCCCCC      750

GCCTGCGGTC  CCATCAGAGC  AGGCCTCGGT  TGGGTACGGG  ACGGTCCTCG      800

CTCGCACCCC  TACAATTTTC  CTGCAGGCTC  GGGGGGCTCT  ATTCTCCGCT      850

CTTCCTCCAC  CCCGTGCAGG  GCACGGTACC  GGTGGACTTG  GCATCAAGGC      900

AGGAAGAAGA  GGAGCAGTCG  CCCGACTCCA  CAGAGGAAGA  ACCAGTGACT      950

CTCCCAAGGC  GCACCACCAA  TGATGGATTC  CACCTGTTAA  AGGCAGGAGG     1000

GTCATGCTTT  GCTCTAATTT  CAGGAACTGC  TAACCAGGTA  AAGTGCTATC     1050

GCTTTCGGGT  GAAAAGAAC   CATAGACATC  GCTACGAGAA  CTGCACCACC     1100

ACCTGGTTCA  CAGTTGCTGA  CAACGGTGCT  GAAAGACAAG  GACAAGCACA     1150

AATACTGATC  ACCTTTGGAT  CGCCAAGTCA  AAGGCAAGAC  TTTCTGAAAC     1200

ATGTACCACT  ACCTCCTGGA  ATGAACATTT  CCGGCTTTAC  AGCCAGCTTG     1250

GACTTCT                                                        1257
```